US007879912B2

(12) United States Patent
Martinez et al.

(10) Patent No.: US 7,879,912 B2
(45) Date of Patent: Feb. 1, 2011

(54) PROCESS FOR PREPARING 3,3-DIARYLPROPYLAMINES

(75) Inventors: Maria Angeles Conde Martinez, Oleiros (ES); Ignasi Auqueri Pedemonte, Girona (ES)

(73) Assignee: Medichem S.A., Celrà (ES)

( * ) Notice: Subject to any disclaimer, the term of this patent is extended or adjusted under 35 U.S.C. 154(b) by 555 days.

(21) Appl. No.: 11/945,773

(22) Filed: Nov. 27, 2007

(65) Prior Publication Data

US 2008/0188684 A1 Aug. 7, 2008

Related U.S. Application Data

(63) Continuation-in-part of application No. PCT/IB2006/003498, filed on May 30, 2006.

(60) Provisional application No. 60/685,457, filed on May 27, 2005.

(51) Int. Cl.
*A61K 31/35* (2006.01)
*C07C 215/54* (2006.01)

(52) U.S. Cl. ................................ 514/648; 564/316

(58) Field of Classification Search .................. None
See application file for complete search history.

(56) References Cited

U.S. PATENT DOCUMENTS 5,382,600 A 1/1995 Joensson et al.
7,393,874 B2 * 7/2008 Reddy et al. ................ 514/648

FOREIGN PATENT DOCUMENTS

| EP | 1 693 361 | 8/2006 |
| WO | WO 2004/078700 | 9/2004 |
| WO | WO 2005/061432 | 7/2005 |
| WO | WO 2006/074478 | 7/2006 |

* cited by examiner

*Primary Examiner*—Karl J Puttlitz
(74) *Attorney, Agent, or Firm*—Frommer Lawrence & Haug LLP

(57) ABSTRACT

Described is a process of preparing a pure solid or crystalline racemic 3,3-diarylpropylamine compound and the compounds formed thereof. The solid and crystalline forms of racemic 3,3-diarylpropylamine compound are especially suitable for producing highly pure 3,3-diarylpropylamine salts such as tolterodine tartrate. Also described are the highly pure solid or crystalline forms of racemic tolterodine, racemic tolterodine salt and tolterodine tartrate.

8 Claims, 6 Drawing Sheets

PROCESS FOR PREPARING 3,3-DIARYLPROPYLAMINES

REFERENCE TO RELATED APPLICATIONS

This application is a continuation-in-part of International Patent Application PCT/IB2006/003498, filed May 30, 2006 which published as WO 2007/046001 on Apr. 26, 2007, and which claims priority to U.S. Provisional Application No. 60/685,457, filed May 27, 2005.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised" "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

FIELD OF THE INVENTION

The invention relates to a process for preparing pure solid or crystalline racemic 3,3-diarylpropylamines as a precursor for production of 3,3-diarylpropylamine salts. The invention also relates to the preparation of pure solid or crystalline racemic tolterodine in its free base form as a precursor for production of tolterodine tartrate. Tolterodine tartrate is a commercially marketed pharmaceutically active substance approved by the FDA, under the trademark Detrol®, for the treatment of urinary incontinence.

BACKGROUND OF THE INVENTION

U.S. Pat. No. 5,382,600 involves crude forms of racemic 3,3-diarylpropylamine as having formula I:

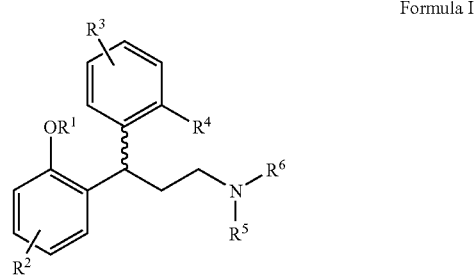

Formula I wherein $R^1$ is hydrogen or methyl, $R^2$, $R^3$ and $R^4$ independently are hydrogen, methyl, methoxy, hydroxy, carbamoyl, sulphamoyl or halogen and $R^5$ and $R^6$ independently are $C_1$-$C_6$ alkyl, which may be joined to form a non-aromatic ring having no heteroatom other than the amine nitrogen and each of which may carry a hydroxy substituent or adamantyl, and wherein $R^5$ and $R^6$ together contain at least four carbon atoms and include the salts formed with physiologically acceptable acids.

Chemically, tolterodine tartrate is (R)—N,N-diisopropyl-3-(2-hydroxy-5-methylphenyl)-3-phenylpropanamine L-hydrogen tartrate, also known as 2-((R)-3-di-isopropylamino-1-phenyl-propyl)-4-methyl-phenol (2R,3R)-2,3-dihydroxybutanedioate having structural Formula Ia; see U.S. Pat. No. 5,382,600.

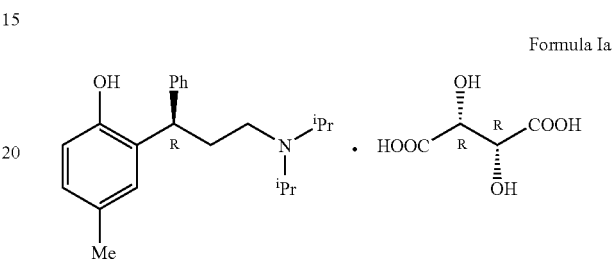

Formula Ia

A process for preparing tolterodine was mentioned in U.S. Pat. No. 5,382,600. The process starts from 6-methyl-4-phenyl-3,4-dihydrocoumarin of structural Formula II.

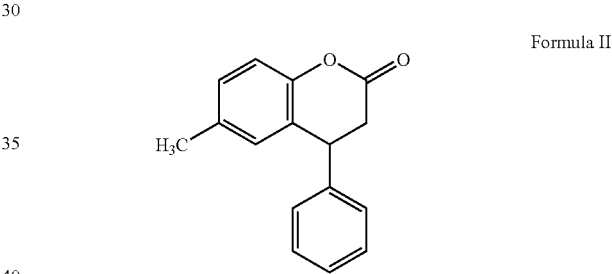

Formula II which by a sequence of reactions is converted into racemic tolterodine HCl ¼H$_2$O (see Example 9c of U.S. Pat. No. 5,382,600). According to Example 22 of U.S. Pat. No. 5,382,600 the racemic tolterodine HCl ¼H$_2$O is resolved with L-(+) tartaric acid to give crude (R)-tolterodine L-hydrogen tartrate which must be recrystallized twice from EtOH to yield "pure" (R)-tolterodine L-hydrogen tartrate having $[\alpha]^{25}_{546}$ (5%, MeOH) of +36.0°.

U.S. Pat. No. 5,922,914 refers to an alternative process for the preparation of tolterodine. According to Examples 4 or 5 of U.S. Pat. No. 5,922,914 racemic tolterodine HCl is basified and extracted in organic solvent resulting in racemic tolterodine base. The organic solvent is evaporated to yield a residue (i.e. not a solid or crystalline form) of racemic tolterodine base. The residue of racemic tolterodine base is then dissolved in ethanol and treated with L-(+) tartaric acid to give crude (R)-tolterodine L-hydrogen tartrate which must be recrystallized twice from EtOH or from MeOH/acetone to yield "pure" (R)-tolterodine L-hydrogen tartrate having [α] (1%, MeOH) of +27.4°.

International patent application WO 01/49649 refers to a process for the enantioselective preparation of tolterodine, which consists of the preparation of an enantiomerically enriched compound of formula II (as described above), starting from a compound of formula III and performing an enantioselective reduction to obtain an enantiomerically enriched compound of formula IV, which by means of a sigmatropic rearrangement is converted to an enantiomerically enriched compound of formula V, which is finally oxidized by means of a Baeyer-Villiger reaction to yield an enantiomerically enriched compound of formula II.

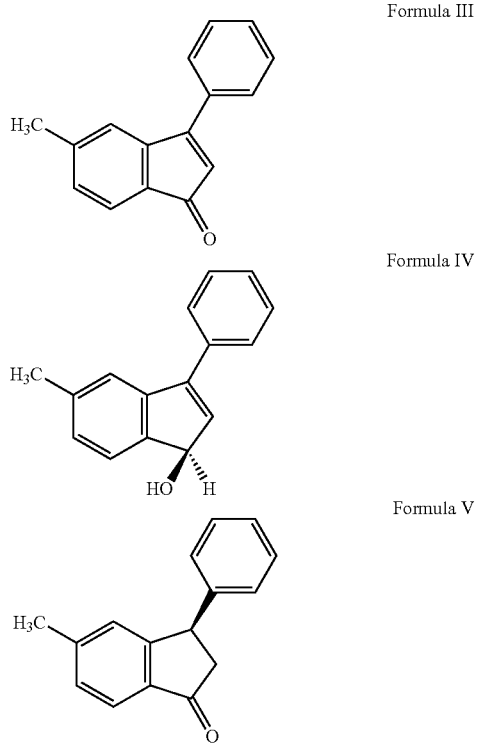

Formula III

Formula IV

Formula V

Examples 4, 5 and 6 of WO 2004/078700 refer to a conversion of tolterodine HBr into crude tolterodine tartrate which is recrystallized from MeOH to yield pure (R)-tolterodine L-hydrogen tartrate e, but discloses no data regarding its enantiomeric purity. It is recognized in the art that (R)-tolterodine L-hydrogen tartrate shows polymorphism (see WO 04/089281).

U.S. Pat. No. 6,822,119 refers to an improved process for the preparation of tolterodine. The process starts from a compound of formula II as described above (6-methyl-4-phenyl-3,4-dihydrocoumarin—referred to as 3,4-dihydro-6-methyl-4-phenyl-2H-benzopyran 2-one in the '119 patent), which by a sequence of reactions is converted into racemic tolterodine HBr. However, there is no mention about the resolution of racemic tolterodine HBr for producing (R)-tolterodine L-hydrogen tartrate.

International patent application WO 05/005356 involves the preparation of tolterodine base isomer by enantioselective hydrogenation of a precursor thereof. A preferred embodiment of that patent application is the preparation of enantiomerically enriched compound of formula II as described above starting with 6-methyl-4-phenylcoumarin.

Racemic forms of 3,3-diarylpropylamine compounds, e.g., tolterodine, have not been obtained with sufficient purity or in crystalline form. Racemic tolterodine in its free base form ("racemic tolterodine") has not been previously obtained with sufficient purity or in crystalline form. As such, the racemic 3,3-diarylpropylamine free base and tolterodine free base have been unsuitable for characterization by X-ray crystallography, differential scanning calorimetry and/or by IR. Additionally, the low degree of purity of these precursor racemic 3,3-diarylpropylamino compounds or racemic tolterodine free base compound results in lower degrees of purity for the (R)-tolterodine L-hydrogen tartrate upon conversion of the precursor compound to the tartrate salt. Accordingly, there are problems in preparing 3,3-diarylpropylamine compounds, e.g., tolterodine.

Citation or identification of any document in this application is not an admission that such document is available as prior art to the present invention.

SUMMARY OF THE INVENTION

The present invention seeks to address problems in preparing 3,3-diarylpropylamine compounds, e.g., tolterodine. Accordingly, the invention provides a process of preparing a pure or substantially pure solid or crystalline racemic 3,3-diarylpropylamine from a salt of racemic 3,3-diarylpropylamine (e.g., purer than in previous processes).

Another object of the invention is a process of preparing a pure solid or crystalline racemic tolterodine from a salt of racemic tolterodine.

A further object of the invention is a process for obtaining a pure solid or crystalline salt of racemic tolterodine by conversion of tolterodine fumarate. In a still further object of the invention the tolterodine hydrogen fumarate is O-methyl tolterodine hydrogen fumarate.

A yet further object of the invention is a pure or solid crystalline racemic 3,3-diarylpropylamine which is characterized by a powder X-ray diffraction pattern, differential scanning calorimetry (DSC) and by IR.

A still further object of the invention is a pure or solid crystalline racemic tolterodine which is characterized by a powder X-ray diffraction pattern, differential scanning calorimetry (DSC) and by IR.

An object of the invention is also a process of obtaining (R)-tolterodine L-hydrogen tartrate salt from the racemic tolterodine with a high degree of chemical and optical purity.

Another object of the invention is racemic 3,3-diarylpropylamine salt with a high degree of chemical purity.

A still further object of the invention is racemic tolterodine salt with a high degree of chemical purity.

An even further object of the invention is (R)-tolterodine L-hydrogen tartrate salt with a high degree of chemical and optical purity.

Surprisingly, the processes of the invention enable the production of pure solid or crystalline forms of racemic 3,3-diarylpropylamine or tolterodine which had heretofore been unachievable. These highly pure forms of racemic 3,3-diarylpropylamine or tolterodine allow for the production of highly pure salts of the corresponding 3,3-diarylpropylamine or tolterodine. These highly pure salts of 3,3-diarylpropylamine or tolterodine (e.g. (R)-tolterodine L-hydrogen tartrate).

In the application the terms racemic tolterodine, racemic tolterodine base and tolterodine base are referred to as racemic tolterodine in its free base form.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
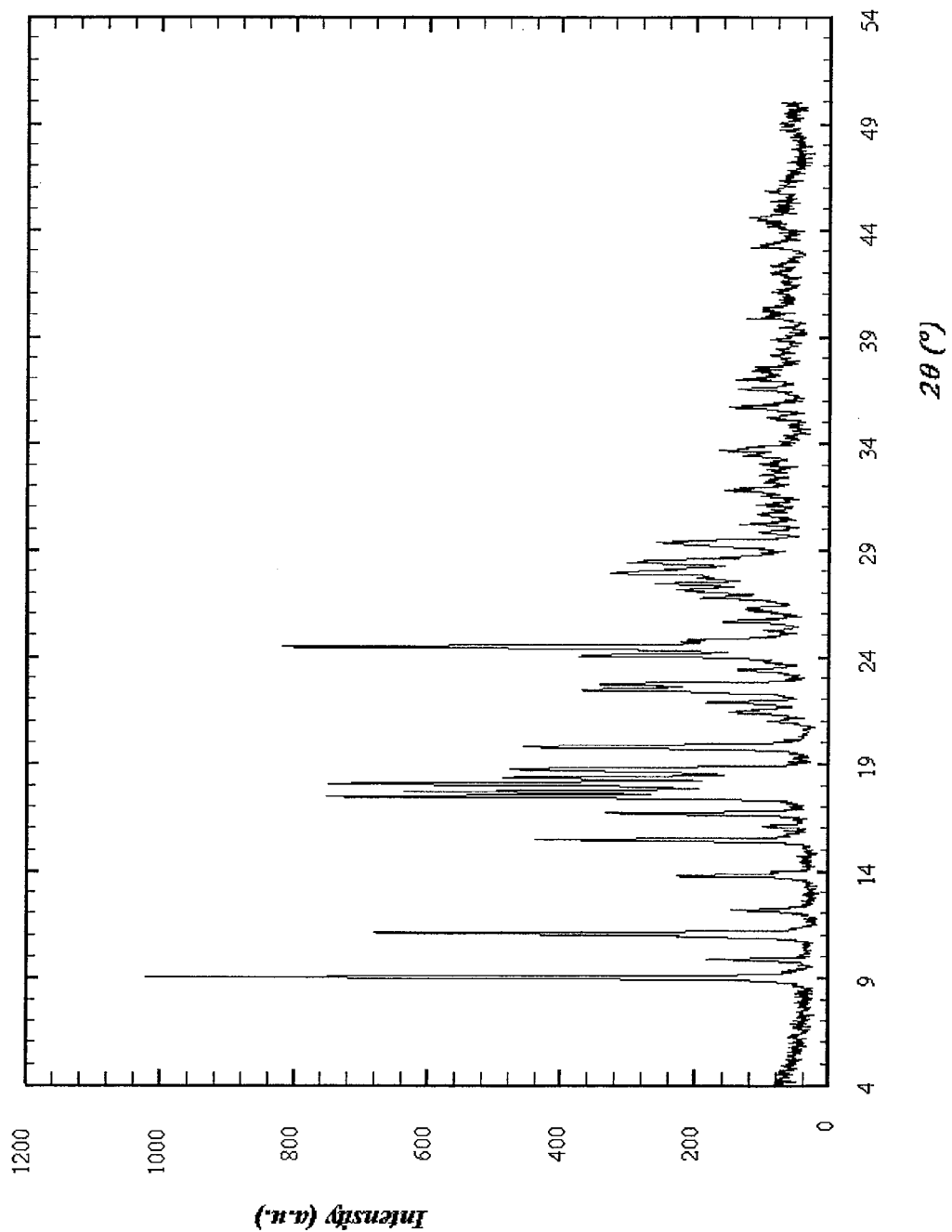
FIG. 1—shows the x-ray diffraction pattern of racemic tolterodine HBr
Figure 2:
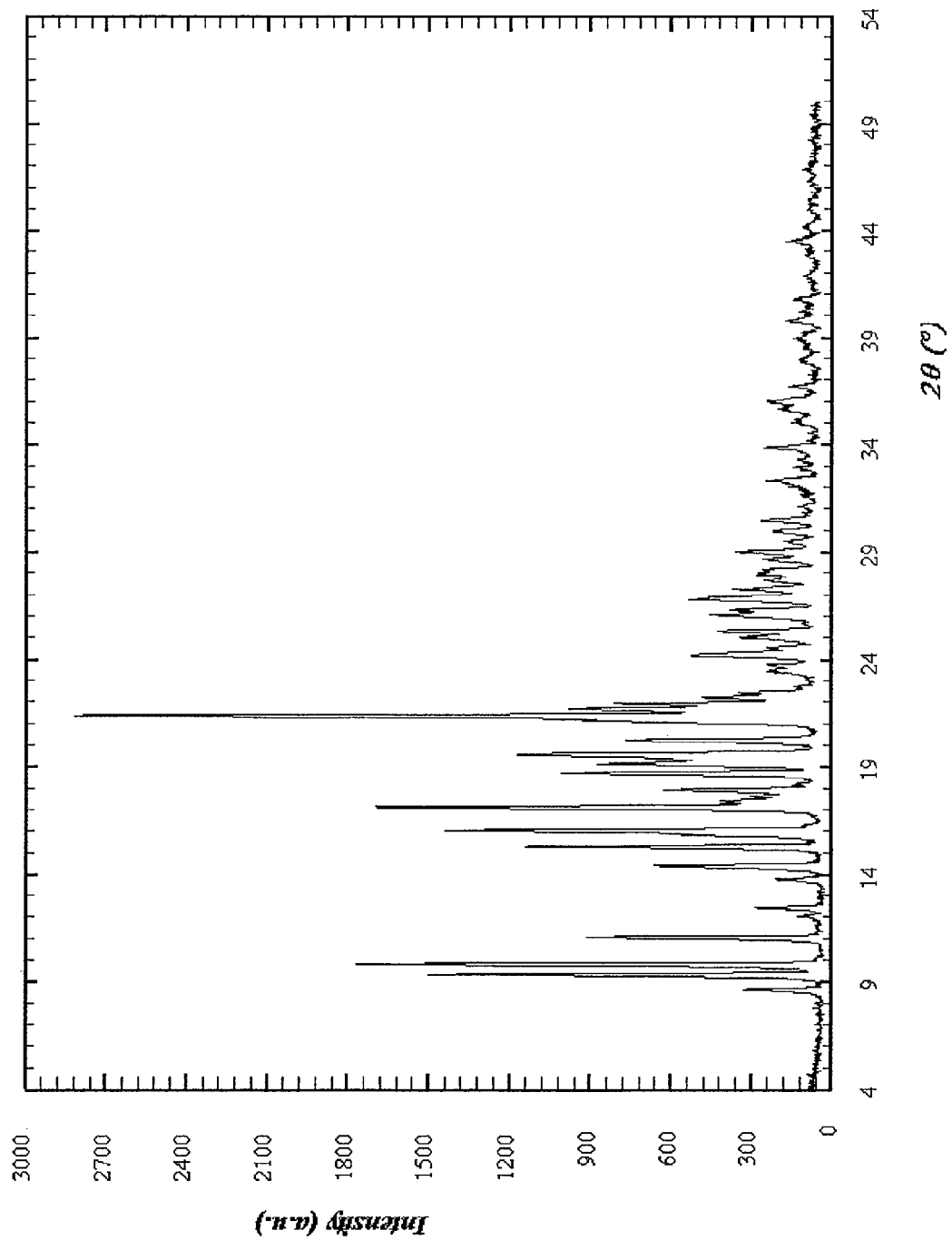
FIG. 2—shows the x-ray diffraction pattern of N,N-diisopropyl-3-(2-methoxy-5-methylphenyl)-3-phenylpropanamine hydrogen fumarate.
Figure 3:
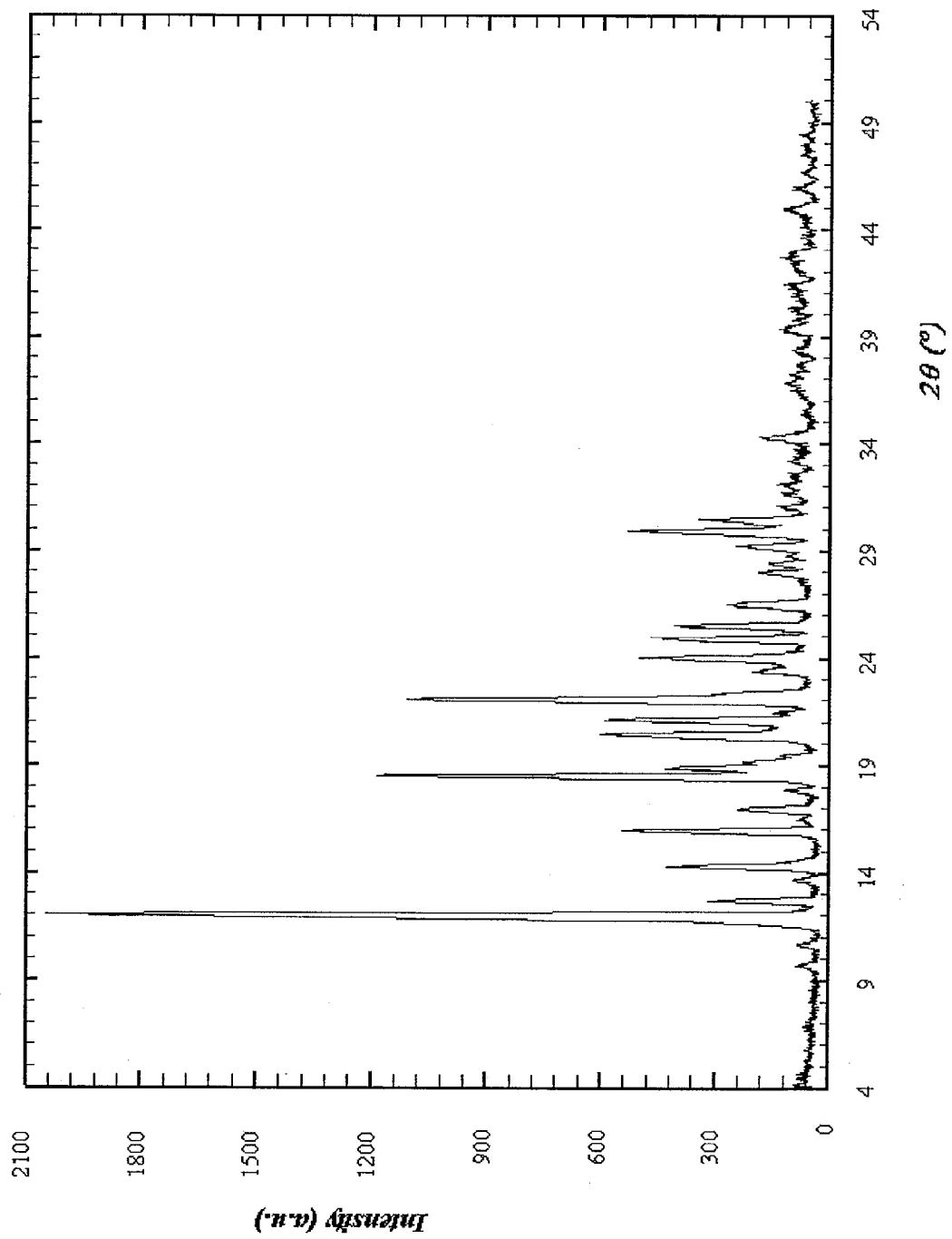
FIG. 3—shows the x-ray diffraction pattern of (R)-tolterodine L-hydrogen tartate obtained according to the present invention.
Figure 4:
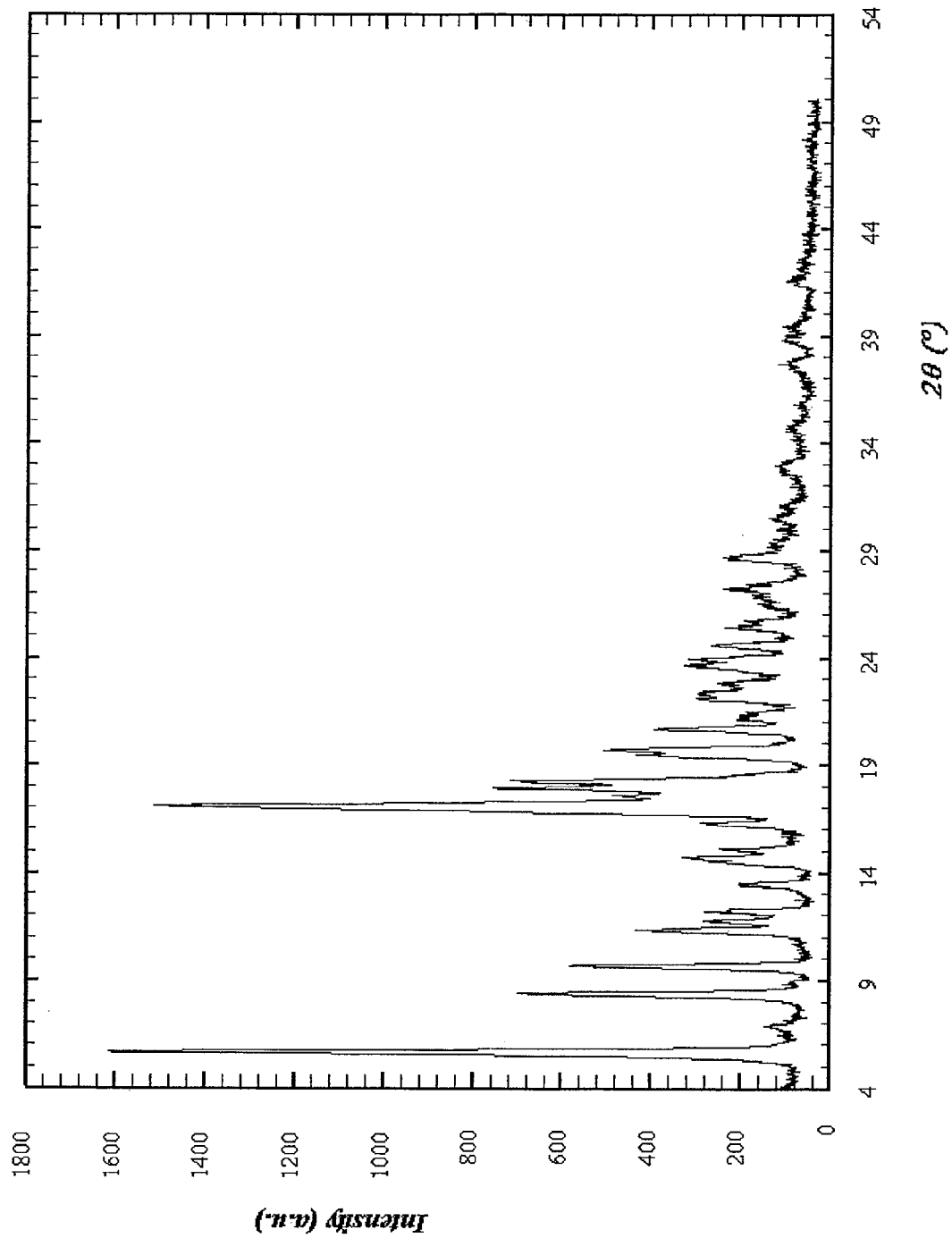
FIG. 4—shows the x-ray diffraction pattern of racemic tolterodine base obtained according to the present invention. $CuK_\alpha$ radiation was used and generated peaks at 5.67, 8.37, 9.66, 11.33, 14.68, 17.04, 17.89, 18.21 and 19.67±0.2 degrees two-theta FIG. 5—shows the IR of racemic tolterodine base obtained according to the present invention.
Figure 5:
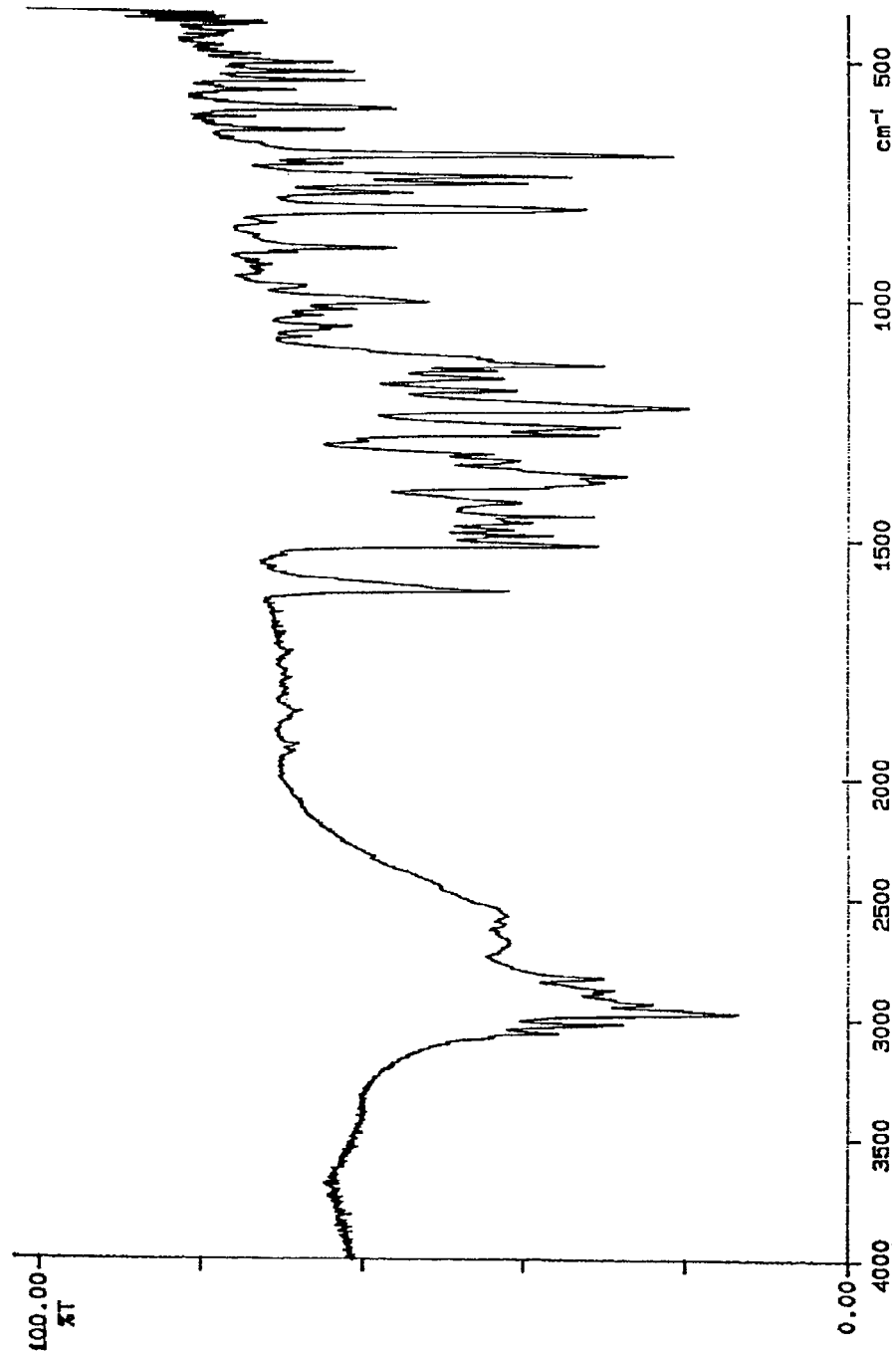
Figure 6:
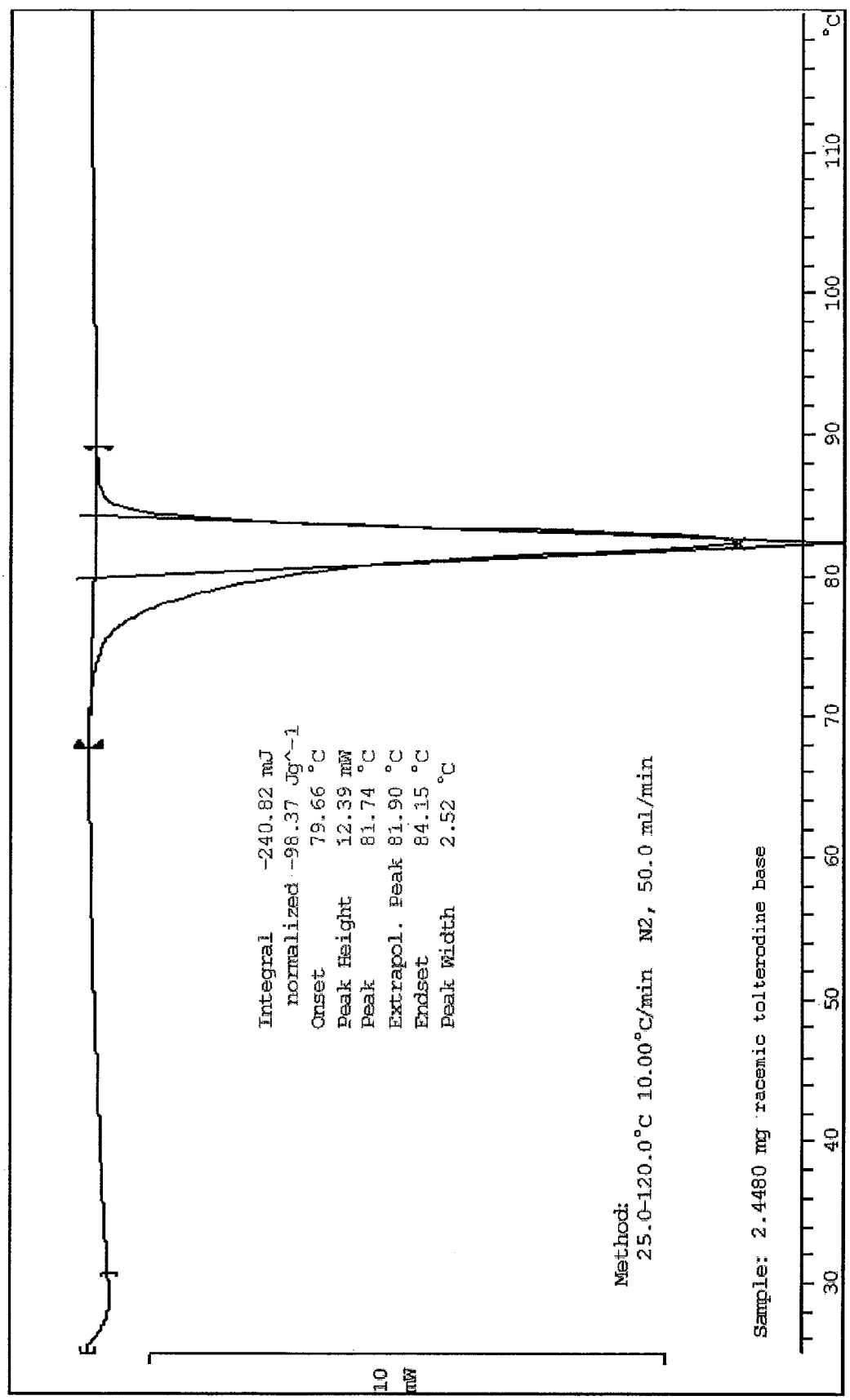
FIG. 6—shows the DSC of racemic tolterodine base obtained according to the present invention.

Racemic 3,3-diarylpropylamine may be obtained by treating any salt of a racemic 3,3-diarylpropylamine with a suitable base for forming the racemic tolterodine free base in an inert solvent optionally with a further purification step. In one embodiment of the invention the 3,3-diarylpropylamine is represented by the formula I:

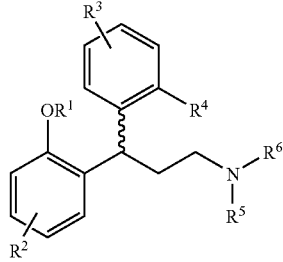

Formula I wherein $R^1$ is hydrogen or $C_1$-$C_6$-alkyl, $R^2$, $R^3$ and $R^4$ independently are hydrogen, $C_1$-$C_6$ alkyl, $C_1$-$C_6$-alkoxy, hydroxy, carbamoyl, sulphamoyl or halogen and $R^5$ and $R^6$ independently are hydrogen or $C_1$-$C_6$ alkyl, which may be joined to form a non-aromatic ring having no heteroatom other than the amine nitrogen and each of which may carry a hydroxy substituent or adamantyl, and include the salts formed with physiologically acceptable acids.

In another embodiment of the invention, the 3,3-diarylpropylamine is represented by the formula I as described above and $R^1$ is hydrogen or $C_1$-$C_4$-alkyl, $R^2$, $R^3$ and $R^4$ independently are hydrogen, $C_1$-$C_4$ alkyl, $C_1$-$C_4$-alkoxy, hydroxy, carbamoyl, sulphamoyl or halogen and $R^5$ and $R^6$ independently are hydrogen or $C_1$-$C_4$ alkyl, which may be joined to form a non-aromatic ring having no heteroatom other than the amine nitrogen and each of which may carry a hydroxy substituent or adamantyl, and include the salts formed with physiologically acceptable acids.

In yet another embodiment of the invention, the 3,3-diarylpropylamine is represented by the formula I as described above and $R^1$ is hydrogen, methyl, or ethyl; $R^2$, $R^3$ and $R^4$ independently are hydrogen, methyl, ethyl, methoxy, or ethoxy, and $R^5$ and $R^6$ independently are $C_1$-$C_4$ alkyl, which may be joined to form a non-aromatic ring having no heteroatom other than the amine nitrogen, and wherein $R^5$ and $R^6$ together contain at least four carbon atoms and include the salts formed with physiologically acceptable acids.

In still another embodiment of the invention, the 3,3-diarylpropylamine is represented by the formula I, wherein $R^1$ is hydrogen or methyl, $R^2$, $R^3$ and $R^4$ independently are hydrogen, methyl and $R^5$ and $R^6$ independently are $C_1$-$C_4$ alkyl.

In another embodiment of the invention the racemic 3,3-diarylpropylamine is racemic tolterodine that may be obtained by treating any salt of racemic tolterodine with a suitable base for forming the racemic tolterodine free base in an inert solvent. Appropriate salts for racemic 3,3-diarylpropylamine or racemic tolterodine are salts recognized by those of skill in the art to be pharmaceutically acceptable salts which include but is not limited to inorganic or organic acids. Salts with inorganic acids include but are not limited to hydrochloric acid, hydrobromic acid, phosphoric acid or sulfuric acid. Salts with organic carboxylic or sulfonic acids include but are not limited to acetic acid, propionic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid or naphthalenedisulfonic acid.

In another embodiment of the invention, the racemic tolterodine are hydrohalic salts, which includes but is not limited to hydrochloric and hydrobromic salts.

The base for forming the racemic tolterodine free base ("racemic tolterodine") is an organic or inorganic base. In one embodiment of the invention, the base includes but is not limited to alkali or alkaline earth metal carbonates, such as sodium carbonate or potassium carbonate; bicarbonates such as sodium bicarbonate or tertiary amines such as triethylamine or diisopropylethylamine. In another embodiment of the invention, the base is sodium hydroxide or potassium hydroxide. In yet another embodiment of the invention, the base is used in an amount which allows to reach a pH value of about 10 to about 12, more preferably about to 11.

The inert solvent is a solvent or a mixture of solvents which allows the precipitation of racemic tolterodine. An inert solvent is understood to be a solvent which does not react substantially with the reactants/compounds in solution. In one embodiment of the invention, the inert solvent is a mixture of water and water miscible organic solvents which includes but is not limited to alcohols such as methanol, ethanol; acetone, ethyl acetate and ethers. In another embodiment of the invention, the mixture of solvent is water and acetone.

According to the present invention there is provided crystalline racemic 3,3-diarylpropylamines or crystalline racemic tolterodine which is characterized by a powder X-ray diffraction pattern, DSC and by IR. This is achieved by purifying the racemic 3,3-diarylpropylamine or racemic tolterodine comprising crystallizing or suspending the racemic 3,3-diarylpropylamine or racemic tolterodine from/with an organic solvent.

In one embodiment of the invention, the optional purification step comprises dissolving the racemic 3,3-diarylpropylamine or racemic tolterodine in an inert organic solvent, heating to reflux, optionally filtering the hot inert organic solution of racemic 3,3-diarylpropylamine or racemic tolterodine, cooling the resulting filtrate and allowing the racemic 3,3-diarylpropylamine or racemic tolterodine to precipitate out of solution. The amount of inert organic solvent for crystallization is the necessary amount to obtain a solution at reflux temperature. In another embodiment of the invention, the inert organic solvent is acetonitrile.

The inert organic solution of racemic 3,3-diarylpropylamine or racemic tolterodine may optionally be treated with a decolorizing agent in order to improve the quality attributes like color, purity, removing related organic compounds and possible sources of residue on ignition in the final product (R)-tolterodine L-hydrogen tartrate. The decolorizing agent can be any conventional decolorizing agent, including but not limited to, alumina, activated alumina, silica and charcoal. The decolorization temperature is preferably between about room temperature and about 60° C. Alternatively, the organic solution of racemic tolterodine base may optionally be filtered in order to improve the quality attributes like the absence of insolubles in the organic solvent. In another embodiment of the invention, the filtration temperature is between about room temperature and about 60° C.

The crystalline racemic 3,3-diarylpropylamine or crystalline racemic tolterodine is generally provided in a substantially pure form. In one embodiment of the invention, the crystalline racemic tolterodine has a chemical purity measured by HPLC of greater than about 90%. In another embodiment of the invention, the chemical purity is greater than about 95%. In yet another embodiment of the invention, the chemical purity is greater than about 98%. In still another embodiment of the invention, the chemical purity is greater than about 99%.

The salts of racemic tolterodine used to make the racemic tolterodine (e.g. tolterodine hydrochloride or hydrobromide), can be obtained according to the procedures described in the literature. For example following example 9c of U.S. Pat. No. 5,382,600, or the single example of U.S. Pat. No. 6,822,119, step e. However, in one embodiment of the invention, N,N-diisopropyl-3-(2-methoxy-5-methylphenyl)-3-phenylpropanamine in its form of fumarate salt ("O-methyl tolterodine hydrogen famarate") instead of in its free base form is used. The O-methyl tolterodine hydrogen fumarate salt can be used to form other tolterodine salts as defined above. In one embodiment of this invention, O-methyl tolterodine hydrogen fumarate is reacted in the presence of one or more organic or inorganic acids to form acid salt form of tolterodine. In yet another embodiment of the invention, the O-methyl tolterodine hydrogen fumarate is reacted in the presence of glacial acetic acid and hydrobromic acid to form tolterodine hydrobromide. The resulting chemical purity as measured by HPLC of the tolterodine salt formed from O-methyl tolterodine hydrogen fumarate ranges from about 85% to about 95%. In another embodiment of the invention, the chemical purity is about 88% to about 92%. In yet another embodiment of the invention, the chemical purity is about 90.5%. These substantially pure forms of tolterodine salt are also suitable for characterization by X-ray crystallography.

The crystalline racemic 3,3-diarylpropylamine or crystalline racemic tolterodine obtained may optionally be converted to a pharmaceutically acceptable salt. In one embodiment of the invention, the pharmaceutically acceptable salt is a (R)-tolterodine L-hydrogen tartrate salt. The method of preparing the tartrate salt of 3,3-diarylpropylamine or tolterodine comprises reacting crystalline racemic tolterodine with L-(+)-tartaric acid in an inert organic solvent or mixture of inert solvents.

In one embodiment of the invention, crystalline racemic 3,3-diarylpropylamine or crystalline racemic tolterodine is reacted with L-tartaric acid in an alcohol which includes but is not limited to methanol and ethanol. In another embodiment of the invention, the organic solvent is ethanol. The obtained (R)-tolterodine L-hydrogen tartrate is then purified by suspension or recrystallization from an organic solvent. In one embodiment of the invention, the organic solvent is an alcohol solvent or a mixtures of alcohol solvents. In another embodiment of the invention, a two step recrystallization process is performed wherein the first step uses a first recrystallization solvent or mixture of solvents and the second step uses a second recrystallization solvent or mixture of solvents. The first and second recrystallization solvents or mixtures thereof can be different or the same; when the same, the second solvent or mixtures thereof refers to use of fresh solvent. The recrystallization solvents are selected from the organic solvents described above. In another embodiment of the invention, the first recrystallization solvent is a mixture of methanol and ethanol. The resulting 3,3-diarylpropylamine or R)-tolterodine L-hydrogen tartrate salt compounds obtained by the methods described above have a high degree of chemical and optical purity. In one embodiment of the invention, the (R)-tolterodine L-hydrogen tartrate compounds of the invention have a degree of chemical purity in the range of about 99.85% to about 99.99% and an optical purity of about 99.50% to about 99.99%. In another embodiment of the invention, the (R)-tolterodine L-hydrogen tartrate compounds of the invention have a degree of chemical purity in the range of about 99.90% to about 99.95% and an optical purity of about 99.60% to about 99.70%.

The invention will now be further described by way of the following non-limiting examples.

EXAMPLES

Reference to HPLC purity is defined by the methods described below:

HPLC Method for the Assessment of Chemical Purity:

The chromatographic separation is carried out in a Kromasil C8, 5 μm. 25 cm×4.6 mm. I.D column.

The mobile phase is prepared by mixing 470 ml of acetonitrile with 530 ml of pH=3.0 buffer, which is prepared from 0.592 g $KH_2PO_4$ and 1.01 g of 1-pentanesulfonic acid sodium salt dissolved in 530 ml of water, adjusting the pH to 3.0 with 10% orthophosphoric acid. This mobile phase is mixed and filtered through 0.22 μm nylon filter under vacuum.

The chromatograph is equipped with a 215 nm detector and the flow rate is 1.3 ml per minute at room temperature. 20 μl of a test sample is injected into the HPLC. The test sample is prepared dissolving the appropriate amount of sample to obtain 2 mg per ml of mobile phase.

HPLC Method for the Assessment of Optical Purity:

The chromatographic separation is carried out in a Chiralcel OD-H (5 μm) 4.6 mm.×25 cm. I.D column.

The mobile phase is prepared by mixing 20 volumes of isopropyl alcohol with 980 volumes of n-hexane, and the adding 0.6 ml of trifluoroacetic acid and 1 ml of diethylamine. This mobile phase is mixed and filtered through 0.22 μm nylon filter under vacuum.

The chromatograph is equipped with a 284 nm detector and the flow rate is 0.5 ml per minute at room temperature (20-25° C.). 30 μl of a test sample is injected into the HPLC. The test sample is prepared as follows: to 100 mg of (R)-tolterodine L-hydrogen tartrate, accurately weighed, add 50 ml of $H_2O$ and approximately 0.05 ml of NaOH 50%, until the pH of the solution reaches a value of 12. Extract with 50 ml of n-hexane, wash twice with 25 ml of water, dry the organic phase with Na₂SO₄ and filter.

Method to Determine Particle Size

Particle size is measured using a Malvern Mastersizer S particle size analyzer with an MS1 Small Volume Sample Dispersion Unit stirred cell. A 300 RF mm lens and a beam length of 2.4 mm is used. Samples for analysis are prepared by dispersing a weighed amount of tolterodine tartrate (approximately 60 mg) in 20 mL of isopropanol. Deliver dropwise to the previously filled and background corrected measuring cell until the obscuration reaches the desired level. Volume distributions are obtained for three times. Upon measurement completion, the sample cell is emptied, cleaned and refilled with suspending medium. The sampling procedure is then repeated. For characterization, the values of D10, D50 and D90 are specifically listed, each one being the mean of the six values available for each characterization parameter.

Example 1

Preparation of N,N-Diisopropyl-3-(2-hydroxy-5-methylphenyl)-3-phenylpropanamine hydrobronmide (tolterodine hydrobromide)

75 g (164.83 mmol) of N,N-diisopropyl-3-(2-methoxy-5-methylphenyl)-3-phenylpropanamine hydrogen fumarate, 375 ml of glacial acetic acid and 375 ml of hydrobromic acid were mixed together. The mixture was stirred and heated up to 115° C. (reflux temperature), at which point an homogenous solution was formed. The Temperature was maintained at 115° C. for 9 hours and the mixture was cooled down to 25° C. and stirred at this temperature for 60 minutes. The precipitated solid was filtered, charged again into the vessel and suspended with 600 ml of water. The mixture was stirred for 30 minutes at 25° C. and then filtered under vacuum to obtain 88.09 g of wet solid. (l.o.d: 34.20%, corresponds to 57.96 g, 142.61 mmol of tolterodine hydrobromide), yield 86.51%.

HPLC purity: 90.50% (chemical)

Example 2

Preparation of Analytical Sample of N,N-Diisopropyl-3-(2-hydroxy-5-methylphenyl)-3-phenylpropanamine hydrobromide (tolterodine hydrobromide)

18 g (44.53 mmol) of N,N-diisopropyl-3-(2-hydroxy-5-methylphenyl)-3-phenylpropanamine hydrobromide that was obtained from Example 1, 181 ml of acetone and 90.5 ml of water were mixed together. The pH was adjusted to about 11.1 by adding aqueous sodium hydroxide (50%). After cooling down to 2±2° C. the mixture was stirred for 90 minutes.

The white solid that precipitated was filtered and charged again into the vessel and suspended with 180 ml of water. The suspension was stirred for 30 min at 25±5° C., and the white solid was filtered under vacuum. The cake was washed with water and the obtained solid was dissolved in 200 ml of ethyl acetate. The organic phase was washed twice with 200 ml of water.

The aqueous phases were discarded and 3.8 ml (2 equivalents) of HBr solution were added to the ethyl acetate solution. The resulting suspension was stirred for 30 min at 25±5° C. and then filtered under vacuum. The collected white solid was washed with ethyl acetate, charged again into the vessel and suspended with 200 ml of water. The mixture was stirred for 30 minutes at 25° C. and then filtered under vacuum. The obtained solid was dried in a tray oven at 60° C., until constant weight to obtain 14.78 g (36.37 mmol) of tolterodine hydrobromide, yield 81.65%.

| | |
|---|---|
| Assay (HClO₄): | 99.16% |
| Melting point: | 216.5° C.-217.8° C. |
| Water (KF): | 0.04% |
| HPLC purity: | 99.90% (chemical) |

Example 3

Preparation of N,N-Diisopropyl-3-(2-hydroxy-5-methylphenyl)-3-phenylpropanamine (tolterodine base)

Tolterodine hydrobromide (100.33 g, 246.9 mmol), 1000 ml of acetone and 500 ml of water were mixed together. The pH was adjusted to about 11.1 by adding aqueous sodium hydroxide (50%). After cooling down to 2±2° C. the mixture was stirred for 90 minutes.

The white solid that precipitated, was filtered and charged again into the vessel and suspended with 1000 ml of water. The suspension was stirred for 30 minutes at 25±5° C., and the white solid was filtered under vacuum. The cake was washed with water and the obtained solid was dried in a tray oven at 60° C. for 4 h minimum, until constant weight to obtain 73.06 g (224.45 mmol) of tolterodine base, yield 90.92%.

| | |
|---|---|
| Assay: | 99.36% |
| KF: | 0.04% |
| HPLC purity: | 99.06% (chemical) |

Example 4

Purification of tolterodine base to obtain an analytical sample 20 g (61.44 mmol) of tolterodine base (HPLC purity: 99.06%) and 90 ml of acetonitrile were mixed together. The mixture was heated up to 48° C., at which point a homogenous solution was formed. The solution was filtered and cooled down to 0° C. Then it was stirred at this temperature for 60 minutes. The precipitated solid was filtered under vacuum. The cake was washed with 2×2.5 ml of acetonitrile and the obtained solid was dried in a tray oven at 60° C. for 3 h minimum, until constant weight to obtain 17.98 g (55.24 mmol) of tolterodine base, yield 89.9%.

| | |
|---|---|
| Assay: | 99.57% |
| Melting point: | 81.3° C.-81.7° C. |
| KF: | 0.1% |
| HPLC purity: | 99.83% (chemical) |

Example 5

Preparation of (R)—N,N-diisopropyl-3-(2-hydroxy-5-methylphenyl)-3-phenylpropanamine L-hydrogen tartrate (tolterodine tartrate)

42.15 g (129.49 mmol) of (±)—N,N-di-isopropyl-3-(2-hydroxy-5-methylphenyl)-3-phenylpropanamine (racemic tolterodine base) and 422 ml (333 g) of ethanol. were mixed together. The mixture was heated up to 35° C. and filtered to remove any particulates. The clear solution thus obtained was heated up to 62° C. At this point a filtered solution of 19.45 g (129.58 mmol, 1 eq.) of L-tartaric acid in 146.33 g (185 ml) of EtOH was added. The mixture was heated up to 78° C. (reflux temperature) and stirred at this temperature for 30 minutes. Then it was cooled down to 48° C. and stirred at this temperature for 2 hours. The precipitated solid was filtered at 48° C. under vacuum. The cake was washed with 2×6 ml of EtOH to obtain 34.94 g of wet solid (l.o.d: 13.95%, corresponds to 30.06 g of dry material, yield 48.81%).

The isolated solid was charged again into the vessel and 300 ml (238 g) of MeOH were added. The mixture was heated up to reflux and the reflux was maintained for 30 minutes. After cooling down to 55° C., 145 ml of EtOH were added and the mixture was heated again to reflux, and kept for 30 minutes. After that, the mixture was cooled down to 2° C. and stirred at this temperature for 2 hours. The precipitated solid was filtered under vacuum and the cake was washed with 3×2 ml of EtOH to obtain 27.44 g of wet solid (l.o.d: 20.19%, corresponds to 21.89 g of dry material, yield 77%).

The wet solid was charged again into the vessel and 213 ml (169 g) of EtOH were added. The mixture was heated up to reflux and the reflux was maintained for 30 minutes. After cooling down to 37° C. and stirring at that temperature for 30 minutes, the precipitated solid was filtered at that temperature under vacuum. The cake was washed with 3×2 ml of EtOH and the obtained solid was dried in a vacuum tray oven at 60° C. until constant weight. 21.13 g of (R)-tolterodine L-hydrogen tartrate were obtained, overall yield 34.31%.

| | |
|---|---|
| Assay (HClO$_4$): | 100.13% |
| Melting point: | 207.5° C.-208.4° C. |
| Water (KF): | 0.11% |
| Specific rotation: | +28.46° (c = 1; Methanol, 25° C., line D) |
| HPLC purity: | 99.94% (chemical) |
| e.e (by Chiral HPLC): | 99.70% (optical) |

Example 6

Preparation of (R)—N,N-diisopropyl-3-(2-hydroxy-5-methylphenyl)-3-phenylpropanamine L-hydrogen tartrate (tolterodine tartrate)

48.45 g of water wet N,N-diisopropyl-3-(2-hydroxy-5-methylphenyl)-3-phenylpropanamine (tolterodine base) (18.36 g dry equivalent, 56.41 mmol) and 184 ml (148 g) of ethanol were mixed together. A solution was obtained that was filtered to remove any particulates. The solution was heated up to 62° C., at which point a filtered solution of 8.47 g (56.42 mmol, 1 eq.) of L-tartaric acid in 63.63 g (80 ml) of EtOH was added. The mixture was heated up to 78° C. (reflux temperature) and stirred at that temperature for 30 minutes. After cooling down to 17° C. it was stirred for 2 hours. The precipitated solid was filtered under vacuum and the cake was washed with 2×6 ml of EtOH to obtain 15.43 g of wet solid (l.o.d: 24.84%, corresponds to 11.59 g of dry material, yield 43.18%).

The solid was charged again into the vessel and 116 ml (91.67 g) of MeOH were added. The mixture was heated up to reflux at which point a thin suspension was formed and kept at reflux for 30 minutes. After cooling down to 55° C., 58 ml of EtOH were added and the mixture was heated up to reflux again and kept at reflux for 30 minutes. After cooling down to 2° C., it was stirred at this temperature for 2 hours. The precipitated solid was filtered under vacuum and the cake was washed with 3×2 ml of EtOH to obtain 10.91 g of wet solid (l.o.d: 18.09%, corresponds to 8.93 g of dry material, yield 77%).

The solid was charged again into the vessel with 89 ml (71 g) of EtOH and the mixture was heated up to reflux, the reflux was maintained for 30 minutes and the mixture was cooled down to 37° C., stirred for 30 minutes and filtered at 37° C. under vacuum. The cake was washed with 3×2 ml of EtOH and the obtained solid was dried in a vacuum tray oven at 60° C. until constant weight. 9.26 g of (R)-tolterodine L-hydrogen tartrate were obtained, overall yield 34.52%.

| | |
|---|---|
| Assay (HClO$_4$): | 100.41% |
| Melting point: | 212.2° C.-212.6° C. |
| Water (KF): | 0.07% |
| Specific rotation: | +28.27° (c = 1; Methanol, 25° C., line D) |
| HPLC purity: | 99.90% (chemical) |
| e.e. (by chiral HPLC): | 99.64% (optical) |

When scaling up example 6 (R)-tolterodine L-hydrogen tartrate, the following analytical data was obtained:

| | |
|---|---|
| Assay (HClO$_4$): | 100.19% |
| Water (KF): | 0.14% |
| Specific rotation: | +28.27° (c = 1; Methanol, 25° C., line D) |
| HPLC purity: | 99.94% (chemical) |
| e.e. (by chiral HPLC): | 100% (optical) |
| Particle size: | D (v, 0.1) = 9.0 µm; D (v, 0.5) = 33.7 µm; D (v, 0.9) = 77.7 µm. |

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. Isolated solid or crystalline racemic tolterodine having a powder X-ray diffraction pattern generated using CuK$_\alpha$ radiation with peaks at 5.67, 8.37, 9.66, 11.33, 14.68, 17.04, 17.89, 18.21 and 19.67±0.2 degrees two-theta.

2. The isolated solid or crystalline racemic tolterodine of claim 1 having a chemical purity of at least about 90%.

3. The isolated solid or crystalline racemic tolterodine of claim 1 having a chemical purity of at least about 95%, .

4. The isolated solid or crystalline racemic tolterodine of claim 1 having a chemical purity of at least about 98%.

5. The isolated solid or crystalline racemic tolterodine of claim 1 having a chemical purity of at least about 99%.

6. The isolated solid or crystalline racemic tolterodine of claim 1 having a chemical purity of about 99.50% to about 99.99%.

7. The isolated solid or crystalline racemic tolterodine of claim 1 having a chemical purity of about 99.60% to about 99.70%.

8. The isolated solid or crystalline racemic tolterodine of claim 1 having a particle size distribution wherein 10% of the total volume is made of particles having a diameter below 10 µm, 50% of the total volume is made of particles having a diameter below 35 µm and 90% of the total volume is made of particles having a diameter below 80 µm.

* * * * *